United States Patent
Alie et al.

(10) Patent No.: US 9,987,661 B2
(45) Date of Patent: Jun. 5, 2018

(54) BIASING OF CAPACITIVE MICROMACHINED ULTRASONIC TRANSDUCERS (CMUTS) AND RELATED APPARATUS AND METHODS

(71) Applicant: Butterfly Network, Inc., Guilford, CT (US)

(72) Inventors: Susan A. Alie, Stoneham, MA (US); Jaime Scott Zahorian, Guilford, CT (US); Kailiang Chen, Guilford, CT (US)

(73) Assignee: Butterfly Network, Inc., Guilford, CT (US)

( * ) Notice: Subject to any disclaimer, the term of this patent is extended or adjusted under 35 U.S.C. 154(b) by 235 days.

(21) Appl. No.: 14/957,098

(22) Filed: Dec. 2, 2015

(65) Prior Publication Data

US 2017/0157646 A1    Jun. 8, 2017

(51) Int. Cl.
*B06B 1/06* (2006.01)
*B06B 1/02* (2006.01)

(52) U.S. Cl.
CPC .............. *B06B 1/02* (2013.01); *B06B 1/0292* (2013.01)

(58) Field of Classification Search
CPC ....... B06B 1/02; B06B 1/0207; B06B 1/0292; H02N 2/00; A61B 8/00; A61B 8/14; H04R 19/00; H04R 19/005
See application file for complete search history.

(56) References Cited

U.S. PATENT DOCUMENTS

| | | | |
|---|---|---|---|
| 5,286,671 A | 2/1994 | Kurtz et al. | |
| 6,328,696 B1 | 12/2001 | Fraser | |
| 6,381,197 B1 * | 4/2002 | Savord | B06B 1/0292 367/178 |
| 6,430,109 B1 | 8/2002 | Khuri-Yakub et al. | |
| 6,443,901 B1 | 9/2002 | Fraser | |
| 6,645,145 B1 | 11/2003 | Dreschel et al. | |
| 6,659,954 B2 | 12/2003 | Robinson | |
| 6,694,817 B2 | 2/2004 | Degertekin et al. | |
| 6,779,387 B2 | 8/2004 | Degertekin | |

(Continued)

FOREIGN PATENT DOCUMENTS

| | | |
|---|---|---|
| GB | 2 467 776 A | 8/2010 |
| KR | 10-2013-0134724 A | 12/2013 |

(Continued)

OTHER PUBLICATIONS

[No Author Listed], Sil-Via, TSI & Advanced Features. Silex Microsystems. http://www.silexmicrosystems.com/mems-foundry/sil-via-tsi-advanced-features/ [last accessed Jan. 6, 2015]. 4 pages.

(Continued)

*Primary Examiner* — Edgardo San Martin
(74) *Attorney, Agent, or Firm* — Wolf, Greenfield & Sacks, P.C.

(57) ABSTRACT

Electrical biasing of ultrasonic transducers of an ultrasound device is described. The ultrasonic transducers may be capacitive micromachined ultrasonic transducers (CMUTs). The ultrasonic transducers may be grouped together, with the different groups receiving different bias voltages. The bias voltages for the various groups of ultrasonic transducers may be selected to account for differences between the groups.

12 Claims, 5 Drawing Sheets

(56) References Cited

U.S. PATENT DOCUMENTS

| | | |
|---|---|---|
| 6,795,374 B2 | 9/2004 | Barnes et al. |
| 6,831,394 B2 | 12/2004 | Baumgartner et al. |
| 6,865,140 B2 | 3/2005 | Thomenius et al. |
| 6,958,255 B2 | 10/2005 | Khuri-Yakub et al. |
| 7,030,536 B2 | 4/2006 | Smith et al. |
| 7,037,746 B1 | 5/2006 | Smith et al. |
| 7,052,464 B2 | 5/2006 | Wodnicki |
| 7,104,129 B2 | 9/2006 | Nasiri et al. |
| 7,125,383 B2 | 10/2006 | Hoctor et al. |
| 7,247,246 B2 | 7/2007 | Nasiri et al. |
| 7,250,353 B2 | 7/2007 | Nasiri et al. |
| 7,257,051 B2 | 8/2007 | Thomenius et al. |
| 7,285,897 B2 | 10/2007 | Fisher et al. |
| 7,312,440 B2 | 12/2007 | Degertekin et al. |
| 7,313,053 B2 | 12/2007 | Wodnicki |
| 7,375,420 B2 | 5/2008 | Fisher et al. |
| 7,441,321 B2 | 10/2008 | Baumgartner et al. |
| 7,441,447 B2 | 10/2008 | Degertekin et al. |
| 7,442,570 B2 | 10/2008 | Nasiri et al. |
| 7,451,651 B2 | 11/2008 | Woychik et al. |
| 7,518,251 B2 | 4/2009 | Fisher et al. |
| 7,530,952 B2 | 5/2009 | Huang et al. |
| 7,545,012 B2 | 6/2009 | Smith et al. |
| 7,557,342 B2 | 7/2009 | Federov et al. |
| 7,564,172 B1 | 7/2009 | Huang |
| 7,612,483 B2 | 11/2009 | Degertekin |
| 7,612,635 B2 | 11/2009 | Huang |
| 7,615,834 B2 | 11/2009 | Khuri-Yakub et al. |
| 7,622,848 B2 | 11/2009 | Lee et al. |
| 7,637,149 B2 | 12/2009 | Degertekin et al. |
| 7,646,133 B2 | 1/2010 | Degertekin |
| 7,687,976 B2 | 3/2010 | Haider et al. |
| 7,745,248 B2 | 6/2010 | Park et al. |
| 7,759,839 B2 | 7/2010 | Huang |
| 7,764,003 B2 | 7/2010 | Huang |
| 7,779,696 B2 | 8/2010 | Huang |
| 7,846,102 B2 | 12/2010 | Kupnik et al. |
| 7,878,977 B2 | 2/2011 | Mo et al. |
| 7,880,565 B2 | 2/2011 | Huang |
| 7,888,709 B2 | 2/2011 | Lemmerhirt et al. |
| 7,892,176 B2 | 2/2011 | Wodnicki et al. |
| 7,956,510 B2 | 6/2011 | Huang |
| 8,004,373 B2 | 8/2011 | Huang |
| 8,008,105 B2 | 8/2011 | Huang |
| 8,008,835 B2 | 8/2011 | Degertekin |
| 8,018,301 B2 | 9/2011 | Huang |
| 8,076,821 B2 | 12/2011 | Degertekin |
| 8,105,941 B2 | 1/2012 | Huang |
| 8,120,229 B2 | 2/2012 | Huang |
| 8,133,182 B2* | 3/2012 | Wagner ............... A61B 8/4483 310/334 |
| 8,203,912 B2 | 6/2012 | Roest et al. |
| 8,222,065 B1 | 7/2012 | Smeys et al. |
| 8,241,931 B1 | 8/2012 | Antoine et al. |
| 8,247,945 B2 | 8/2012 | Huang |
| 8,277,380 B2 | 10/2012 | Daft et al. |
| 8,309,428 B2 | 11/2012 | Lemmerhirt et al. |
| 8,315,125 B2 | 11/2012 | Lemmerhirt et al. |
| 8,327,521 B2 | 12/2012 | Dirksen et al. |
| 8,334,133 B2 | 12/2012 | Federov et al. |
| 8,345,508 B2 | 1/2013 | Wodnicki et al. |
| 8,345,513 B2 | 1/2013 | Huang |
| 8,363,514 B2 | 1/2013 | Huang |
| 8,372,011 B2 | 2/2013 | Degertekin |
| 8,398,554 B2 | 3/2013 | Degertekin |
| 8,399,278 B2 | 3/2013 | Lemmerhirt et al. |
| 8,402,831 B2 | 3/2013 | Kupnik et al. |
| 8,429,808 B2 | 4/2013 | Huang |
| 8,451,693 B2 | 5/2013 | Nikoozadeh et al. |
| 8,483,014 B2 | 7/2013 | Huang |
| 8,526,271 B2 | 9/2013 | Huang |
| 8,559,274 B2 | 10/2013 | Huang |
| 8,563,345 B2 | 10/2013 | Adler et al. |
| 8,647,279 B2 | 2/2014 | Daft et al. |
| 8,658,453 B2 | 2/2014 | Lemmerhirt et al. |
| 8,665,672 B2 | 3/2014 | Soeda et al. |
| 8,852,103 B2 | 10/2014 | Rothberg et al. |
| 8,957,564 B1 | 2/2015 | Hiroe et al. |
| 9,061,318 B2 | 6/2015 | Rothberg et al. |
| 9,067,779 B1 | 6/2015 | Rothberg et al. |
| 9,242,275 B2 | 1/2016 | Rothberg et al. |
| 2004/0160144 A1 | 8/2004 | Daft et al. |
| 2005/0121734 A1 | 6/2005 | Degertekin et al. |
| 2005/0177045 A1 | 8/2005 | Degertekin et al. |
| 2005/0203397 A1 | 9/2005 | Degertekin |
| 2007/0140515 A1* | 6/2007 | Oliver ............... B06B 1/0292 381/174 |
| 2007/0167811 A1 | 7/2007 | Lemmerhirt et al. |
| 2007/0167812 A1 | 7/2007 | Lemmerhirt et al. |
| 2007/0180916 A1 | 8/2007 | Tian et al. |
| 2007/0215964 A1 | 9/2007 | Khuri-Yakub et al. |
| 2008/0194053 A1 | 8/2008 | Huang |
| 2008/0290756 A1 | 11/2008 | Huang |
| 2008/0296708 A1 | 12/2008 | Wodnicki et al. |
| 2008/0308920 A1 | 12/2008 | Wan |
| 2009/0122651 A1 | 5/2009 | Kupnik et al. |
| 2009/0134497 A1 | 5/2009 | Barth et al. |
| 2009/0148967 A1 | 6/2009 | Wodnicki et al. |
| 2009/0176375 A1 | 7/2009 | Benson et al. |
| 2009/0250729 A1 | 10/2009 | Lemmerhirt et al. |
| 2010/0027830 A1 | 2/2010 | Hsu et al. |
| 2010/0063397 A1* | 3/2010 | Wagner ............... A61B 8/4483 600/459 |
| 2010/0225200 A1 | 9/2010 | Kupnik et al. |
| 2011/0084570 A1 | 4/2011 | Soeda et al. |
| 2011/0115333 A1 | 5/2011 | Ezaki |
| 2011/0140224 A1 | 6/2011 | Kropelnicki et al. |
| 2011/0272693 A1 | 11/2011 | Kobayashi et al. |
| 2012/0074509 A1 | 3/2012 | Berg et al. |
| 2012/0129301 A1 | 5/2012 | Or-Bach et al. |
| 2012/0187508 A1 | 7/2012 | Adler et al. |
| 2012/0193719 A1 | 8/2012 | Or-Bach et al. |
| 2012/0248554 A1 | 10/2012 | Klein et al. |
| 2013/0096433 A1 | 4/2013 | Lemmerhirt et al. |
| 2013/0116561 A1 | 5/2013 | Rothberg et al. |
| 2013/0161702 A1 | 6/2013 | Chen |
| 2013/0169110 A1 | 7/2013 | Jeong et al. |
| 2014/0057382 A1 | 2/2014 | Supino et al. |
| 2014/0117809 A1 | 5/2014 | Zemp |
| 2014/0217478 A1 | 8/2014 | Rothberg et al. |
| 2014/0219062 A1 | 8/2014 | Rothberg et al. |
| 2014/0264660 A1 | 9/2014 | Rothberg et al. |
| 2014/0288428 A1 | 9/2014 | Rothberg et al. |
| 2015/0016227 A1* | 1/2015 | Brock-Fisher ....... G01N 29/2406 367/181 |
| 2015/0084053 A1 | 3/2015 | Rothberg et al. |
| 2015/0087991 A1* | 3/2015 | Chen ............... G01S 7/5202 600/459 |
| 2015/0298170 A1 | 10/2015 | Rothberg et al. |
| 2016/0009544 A1 | 1/2016 | Rothberg et al. |
| 2016/0296207 A1* | 10/2016 | Brock-Fisher ........ B06B 1/0292 |
| 2016/0310992 A1* | 10/2016 | Van Rens ............ B06B 1/0292 |
| 2016/0363609 A1* | 12/2016 | Wygant ................ B81B 7/007 |
| 2017/0003384 A1* | 1/2017 | Christiansen ......... B06B 1/0215 |

FOREIGN PATENT DOCUMENTS

| | | |
|---|---|---|
| WO | WO 2009/107940 A2 | 9/2009 |
| WO | WO 2012/017978 A2 | 2/2012 |
| WO | WO 2014/151525 A2 | 9/2014 |

OTHER PUBLICATIONS

Calmes et al., Highly Integrated 2-D Capacitive Micromachined Ultrasonic Transducers. 1999 IEEE Ultrason Symp. 1999;1163-6.

Cha et al., Influences of perforation ratio in characteristics of capacitive micromachined ultrasonic transducers in air. Sensors Actuators A. 2011;171:191-8.

Cheng et al., An Efficient Electrical Addressing Method Using Through-Wafer Vias for Two-Dimensional Ultrasonic Arrays. 2000 IEEE Ultrasonics Symposium. 2000;2:1179-82.

(56) References Cited

OTHER PUBLICATIONS

Cheng et al., Electrical Through-Wafer Interconnects with Sub-PicoFarad Parasitic Capacitance. 2001 Microelectromechan Syst Conf. Aug. 24, 2001;18-21.

Daft et al., Microfabricated ultrasonic transducers monolithically integrated with high voltage electronics. Proc Ultrason Symp. 2004;493-6.

Dixon-Warren, Overview of MEMS microphone technologies for consumer applications. MEMS J. Mar. 8, 2011. http://www.memsjournal.com/2011/03/overview-of-mems-microphone-technologies-for-consumer-applications.html [last accessed Feb. 19, 2014]. 10 pages.

Doody et al., Modeling and Characterization of CMOS-Fabricated Capacitive Micromachined Ultrasound Transducers. J Microelectromech Sys. Feb. 1, 2011;20(1):104-18.

Eccardt et al., Micromachined ultrasound transducers with improved coupling factors from a CMOS compatible process. Ultrasonics. Mar. 2000;38:774-80.

Eccardt et al., Surface micromachined ultrasound transducer in CMOS technology. Proc Ultrason Symp. 1996;959-62.

Gurun et al., Front-end CMOS electronics for monolithic integration with CMUT arrays: circuit design and initial experimental results. Proc Ultrason Symp. 2008;390-3.

Helin et al., Poly-SiGe-based CMUT array with high acoustical pressure. MEMS. 2012 IEEE 25th International Conference on Micro Electro Mechanical Systems. Jan. 29, 2012;305-8.

Kim et al., Design and Test of a Fully Controllable 64×128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

Knight et al., Low Temperature Fabrication of Immersion Capacitive Micromachined Ultrasonic Transducers on Silicon and Dielectric Substrates. IEEE Trans Ultrason Ferroelectr Freq Contr. Oct. 2004;51(10):1324-33.

Kupnik et al., CMUT Fabrication Based on a Thick Buried Oxide Layer. Proc IEEE Ultrason Symp. Oct. 2010;2010:547-550. doi:10.1109/ULTSYM.2010.5935935. Epub Jun. 8, 2012. 10 pages.

Kupnik et al., Wafer-Bonded CMUT Meets CMOS. 2010 CMOS Emerging Technology Workshop. May 21, 2010;1-22.

Lemmerhirt et al., A 32×32 capacitive micromachined ultrasonic transducer array manufactured in standard CMOS. IEEE Trans Ultrason Ferroelectr Freq Control. Jul. 2012;59(7):1521-36. doi: 10.1109/TUFFC.2012.2352.

Lemmerhirt et al., An electronically-scanned CMUT-in-CMOS transducer for hemodialysis vascular access monitoring. Ultrason Symp. 2011 IEEE International Conference. Oct. 18, 2011;2193-6.

Lin et al., Packaging of Large and Low-Pitch Size 2D Ultrasonic Transducer Arrays. MEMS Conf. 2010;508-11.

Lu et al., Investigation of thermal stress influence on CMUT in standard CMOS process. Info Auto. 2009 ICIA International Conference. Jun. 22, 2009;1447-51.

Manzanares et al., Air-coupled MUMPs capacitive micromachined ultrasonic transducers with resonant cavities. Ultrason. 2012;52:482-9.

Nikoozadeh et al., Forward-Looking Intracardiac Ultrasound Imaging Using a 1-D CMUT Array Integrated With Custom Front-End Electronics. IEEE Trans Ultrason Ferroelectr Freq Contr. Dec. 2008;55(12):2651-60.

Noble et al., A cost-effective and manufacturable route to the fabrication of high-density 2D micromachined ultrasonic transducer arrays and (CMOS) signal conditioning electronics on the same silicon substrate. Proc Ultrason Symp. 2001;941-5.

Noble et al., Low-temperature micromachined CMUTs with fully-integrated analogue front-end electronics. Proc Ultrason Symp. 2002;1045-50.

Oralkan et al., Volumetric Imaging Using 2D Capacitive Micromachined Ultrasonic Transducer Arrays (CMUTs): Initial Results. 2002 IEEE Ultrason Symp. 2002;1083-6.

Oralkan et al., Volumetric Ultrasound Imaging Using 2-D CMUT Arrays. IEEE Trans Ultrason Ferroelectr Freq Contr. Nov. 2003;50(11):1581-94.

Park et al., Fabrication of Capacitive Micromachined Ultrasonic Transducers via Local Oxidation and Direct Wafer Bonding. J Microelectromechan Syst. Feb. 2011;20(1):95-103.

Torkkeli et al., Capacitative microphone with low-stress polysilicon membrane and high-stress polysilicon backplate. Sensors and Actuators. 2000;85:116-23.

Tsuji et al., Low Temperature Process for CMUT Fabrication with Wafer Bonding Technique. IEEE Intl Ultrason Symp Proc. 2010;551-4.

Um et al., An Analog-Digital-Hybrid Single-Chip RX Beamformer with Non-Uniform Sampling for 2D-CMUT Ultrasound Imaging to Achieve Wide Dynamic Range of Delay and Small Chip Area. IEEE International Solid-State Circuits Conference. Feb. 12, 2014;426-8.

Wodnicki et al., Multi-Row Linear CMUT Array Using CMUTs and Multiplexing Electronics. Proc Ultrason Symp. 2009;2696-9.

Wolffenbuttel et al., Low-temperature silicon wafer-to-wafer bonding using gold at eutectic temperature. Sensors and Actuators A. 1994;43:223-9.

Wygant et al., Integration of 2D CMUT Arrays with Front-End Electronics for Volumetric Ultrasound Imaging. IEEE Trans Ultrason Ferroelectr Freq Contr. Feb. 2008;55(2):327-42.

Xu et al., Characterization of improved Capacitive Micromachined Ultrasonic Transducers (CMUTS) using ALD high- [Kappa] dielectric isola. MEMS. 2014 IEEE 27th International Conference on Micro Electro Mechanical Systems. Jan. 26, 2014;584-7.

Yu et al., Dual-bottom-electrode CMUT based on standard CMOS process. NEMS. 2001 IEEE International Conference. Feb. 20, 2011;21-4.

Zahorian et al., Single chip CMUT arrays with integrated CMOS electronics: fabrication process development and experimental results. Proc Ultrason Symp. 2008;386-9.

Zhuang et al., Integration of trench-isolated through-wafer interconnects with 2d capacitive micromachined ultrasonic transducer arrays. Sensors Actuators A. 2007;138:221-9.

Zhuang et al., Wafer-bonded 2-D CMUT arrays incorporating through-wafer trench-isolated interconnects with a supporting frame. IEEE Trans Ultrason Ferroelectr Freq Control. Jan. 2009;56(1):182-92. doi: 10.1109/TUFFC.2009.1018.

Invitation to Pay Additional Fees dated Jan. 23, 2017 for Application No. PCT/US2016/064325.

International Search Report and Written Opinion dated Apr. 7, 2017 for Application No. PCT/US2016/064325.

\* cited by examiner

US 9,987,661 B2

BIASING OF CAPACITIVE MICROMACHINED ULTRASONIC TRANSDUCERS (CMUTS) AND RELATED APPARATUS AND METHODS

BACKGROUND

Field

The technology described herein relates to micromachined ultrasonic transducers (CMUTs) and related apparatus and methods.

RELATED ART

Capacitive Micromachined Ultrasonic Transducers (CMUTs) are known devices that include a membrane above a micromachined cavity. The membrane may be used to transduce an acoustic signal into an electric signal, or vice versa. Thus, CMUTs can operate as ultrasonic transducers.

BRIEF SUMMARY

According to an aspect of the application, an ultrasound device is provided, comprising a substrate, a plurality of ultrasonic transducers integrated with the substrate and including a first group of ultrasonic transducers and a second group of ultrasonic transducers, and a plurality of individually electrically controllable bias electrodes including a first bias electrode corresponding to the first group of ultrasonic transducers and a second bias electrode corresponding to the second group of ultrasonic transducers.

According to an aspect of the application, a method of operating an ultrasound device having a substrate and a plurality of ultrasonic transducers integrated with the substrate is provided. The method comprises electrically biasing at a first bias voltage a first bias electrode corresponding to a first group of ultrasonic transducers of the plurality of ultrasonic transducers, and simultaneously with biasing the first bias electrode, electrically biasing at a second bias voltage different than the first bias voltage a second bias electrode corresponding to a second group of ultrasonic transducers of the plurality of ultrasonic transducers.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

According to an aspect of the present application, a segmented biasing scheme is implemented for biasing groups of ultrasonic transducers of an ultrasound device. The ultrasound device may be an ultrasound probe, and may include a plurality of ultrasonic transducers configured to produce and/or detect ultrasound signals. The ultrasonic transducers may be CMUTs. Proper operation of the CMUTs may involve electrically biasing the CMUTs, for example by biasing their membranes. Rather than providing a single bias signal to all the CMUTs, via a common electrode, two or more distinct biasing segments may be created. Thus, different groups of the CMUTs may receive different bias signals, allowing for improved operation.

The aspects and embodiments described above, as well as additional aspects and embodiments, are described further below. These aspects and/or embodiments may be used individually, all together, or in any combination of two or more, as the application is not limited in this respect.

Figure 1:
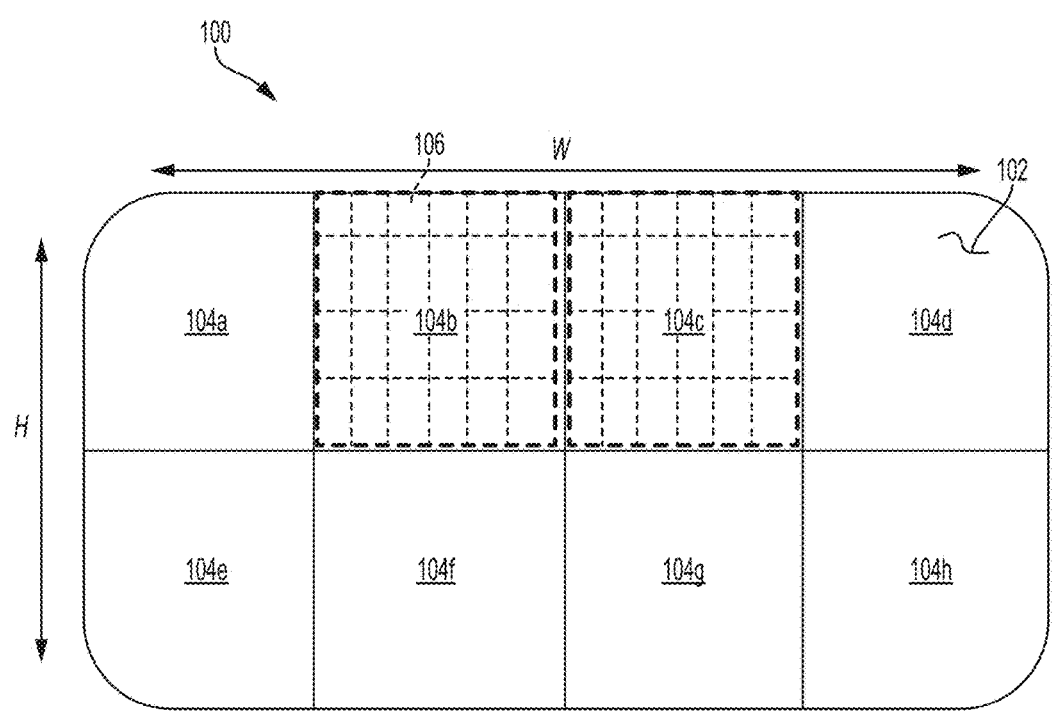
FIG. 1 illustrates a top-down view of an ultrasound device including a plurality of CMUT bias regions, according to a non-limiting embodiment.

FIG. 1 is a top-down view of an ultrasound device according to a first aspect of the present application, in which multiple bias regions are included. The device 100 includes a device surface 102 having a height H and a width W and eight bias regions 104a-104h. The device surface 102 may represent the surface of a substrate such as a semiconductor substrate or a complementary metal oxide semiconductor (CMOS) substrate, and thus may be referred to as a semiconductor device surface in some embodiments. A plurality of CMUTs may be formed in the device surface 102 of device 100. For simplicity of illustration, a plurality of CMUTs 106 are shown for bias regions 104b and 104c simply as dashed boxes since they may not be visible from the top-down view of FIG. 1. In some embodiments, the top surface visible in FIG. 1 may represent a membrane of the CMUTs 106, such as membrane 204 of FIG. 2, described below. However, aspects of the present application are not limited in this respect, and apply equally to other configurations. It should be appreciated that each of the illustrated bias regions 104a-104h may, and in some embodiments does, include one or more CMUTs 106. The bias regions 104a-104h represent separate groups of CMUTs which may be independently electrically biased.

Figure 2:
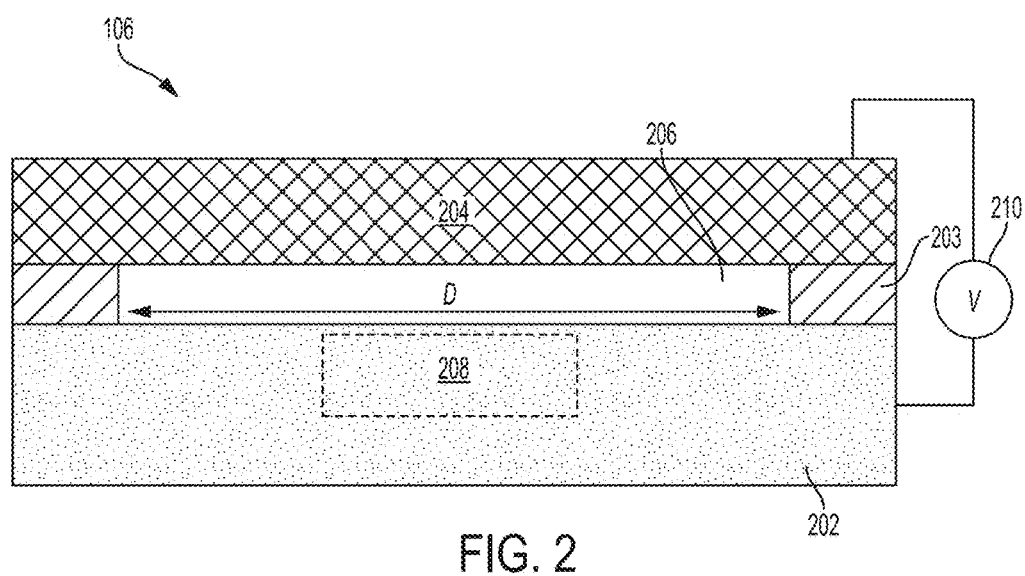
FIG. 2 is a cross-sectional view of a CMUT, according to a non-limiting embodiment.

FIG. 2 is a cross-sectional view of a non-limiting example of a CMUT which may be implemented according to aspects of the present application. The illustrated CMUT may represent the CMUT 106 of FIG. 1. The CMUT 106 includes a substrate 202 and membrane 204 separated by a gap 206 of width (or diameter) D as a result of a standoff 203. The gap 206 may be a vacuum cavity, although alternatives are possible. The diameter D may be microns, tens of microns, hundreds of microns, or any other suitable diameter. Integrated circuitry 208 may optionally be included in the substrate 202. For example, the substrate 202 may be a semiconductor substrate, such as a silicon substrate, and the integrated circuitry 208 may be silicon circuitry. The integrated circuitry 208 may be configured to control operation of the CMUT 106 and/or to detect responses of the CMUTs 106 as described in further detail with respect to FIG. 5.

The CMUT 106 may optionally include additional layers, such as isolation layers, oxides (e.g., silicon oxide), or other layers. These are not illustrated for simplicity, and because the various aspects described herein are not limited to use with any particular type of CMUT.

Figure 3:
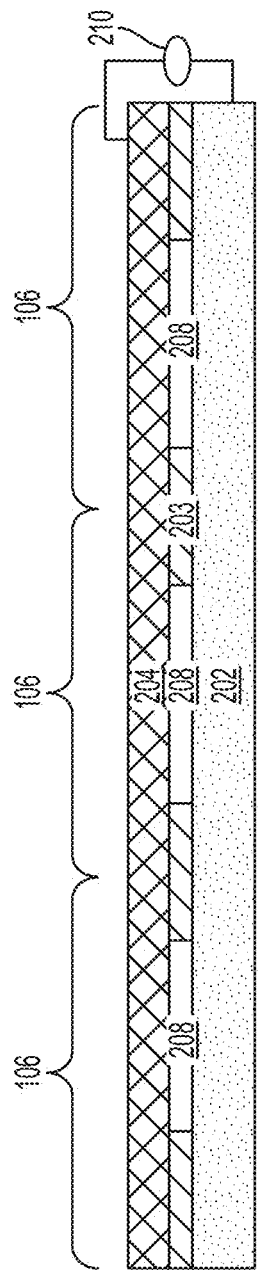
FIG. 3 is a cross-sectional view of a plurality of CMUTs of the type shown in FIG. 2, sharing a common membrane, according to a non-limiting embodiment.

The membrane 204, which may be made of silicon or other suitable material, may be made to vibrate either by applying a voltage to it, such as an alternative current (AC)

voltage, or in response to receiving an ultrasound signal. It may be desirable to apply a direct current (DC) bias signal to the membrane. Such a bias signal can cause so-called "spring softening," or more generally may be used to tune the membrane's ability to vibrate. Thus, application of a suitable bias signal can alter the sensitivity of the CMUT for both transmit and receive mode operation. As shown in FIG. 2, a bias voltage V may be applied by a voltage source 210. The voltage source 210 may be shared by two of more CMUTs 106, and in some embodiments may be integrated with the device 100. FIG. 3 illustrates an example.

In FIG. 3, three CMUTs 106 share the voltage source 210. They also share a common substrate 202 and membrane 204. Thus, a single voltage source 210 may be used to bias all three illustrated CMUTs with a common voltage. It should be appreciated that more than three CMUTs may share a common membrane, and likewise may be biased by a common voltage source. In fact, referring again to FIG. 1, each of the bias regions 104a-104h may represent a group of CMUTs which have a common membrane. The CMUTs for a given bias region may be biased by the same bias signal, but different bias signals may be used for different bias regions. As an example, the CMUTs 106 of bias region 104b may share a common membrane and may be biased by the same bias signal, for example from a voltage source such as voltage source 210. Likewise, the CMUTs 106 of bias region 104c may share a common membrane and may be biased by the same bias signal. However, the bias regions 104b and 104c may be independently biased.

While FIGS. 2 and 3 illustrate application of a bias voltage directly to a CMUT membrane, it should be appreciated that in some embodiments an electrode may be disposed on the membranes. For example, an electrode may be provided on the membrane 204, such that the bias regions 104a-104h may correspond to eight different electrodes configured to bias corresponding groups of CMUTs. In such situations, the separate electrodes may be fabricated by forming a single blanket electrode across the device 100 and then etching the blanket electrode into eight segments corresponding to bias regions 104a-104h. Still, other configurations and manufacturing techniques are possible.

Figure 4:
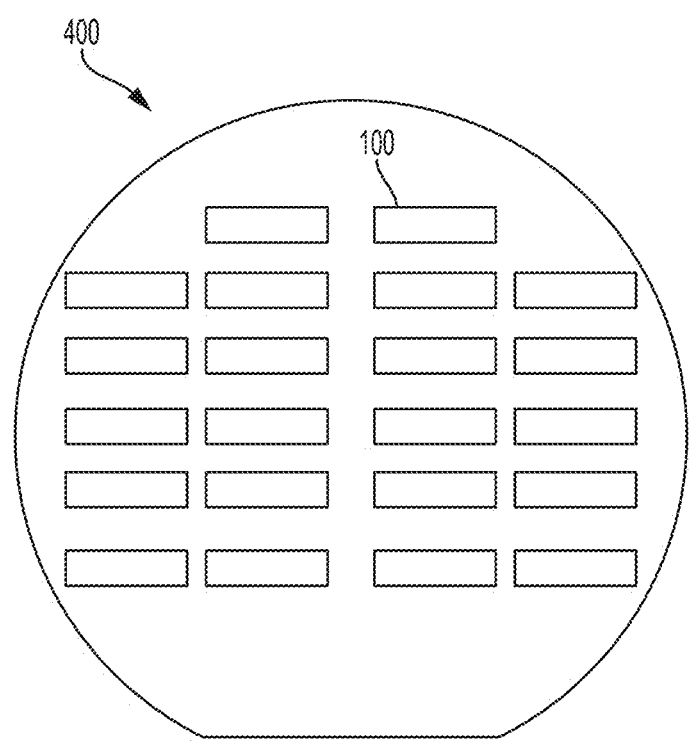
FIG. 4 is a top-down view of a wafer including a plurality of ultrasound devices of the type illustrated in FIG. 1, according to a non-limiting embodiment.

The larger the dimensions H and W, the more beneficial the ability to independently bias different group of CMUTs of an ultrasound device may be. The manufacturing processes used to make CMUTs may result in variations between CMUTs of an ultrasound device. For example, manufacturing many CMUTs on a wafer will typically involve the use of processes such as deposition, lithography, and etching, which may not be applied uniformly across the wafer. Referring to FIG. 4, a wafer 400 may include a plurality of ultrasound devices 100 of the type shown in FIG. 1. Each device 100 may, in some embodiments, be a distinct die. Typical microfabrication steps applied to the wafer 400, such as deposition and etching, may apply differently to devices 100 in the center of the wafer 400 than to devices 100 toward the periphery of the wafer 400. If the dimensions H and W are sufficiently large, then the fabrication steps may apply non-uniformly within a device 100. As non-limiting examples, W may be between 20 mm and 40 mm in some embodiments, may be greater than 10 mm, greater than 20 mm, between 10 mm and 50 mm, or any value or range of values within such ranges. H may be between 2 mm and 10 mm, between 3 mm and 5 mm, greater than 2 mm, or any other value or range of values within such ranges. These dimensions may span tens, hundreds, thousands, or more CMUTs. Standard microfabrication processes may vary over such dimensions. Thus, the CMUTs may be manufactured non-uniformly and may exhibit different inherent operating characteristics. Accordingly, aspects of the present application providing discrete regions of CMUTs which are biased independently may be advantageous.

Referring again to FIG. 1, while approximately twenty CMUTs are shown in relation to each of bias regions 104b and 104c, in practice there may be any suitable number, including many more than are shown. For example, the device 100 may include thousands hundreds of thousands, or millions of CMUTs spread across the width W and height H in an array or other arrangement.

In some embodiments, the difference in bias voltages applied to the different bias regions 104a-104h may be between 3% and 30%, between 5% and 20%, or any value or range of values within such ranges. For example, a bias voltage of approximately 60 volts may be applied to bias region 104a and a bias voltage of approximately 80 volts may be applied to bias region 104d. These, however, are non-limiting examples. In some embodiments, two or more of the bias regions 104a-104h may receive the same bias value. In some embodiments, all the bias regions 104a-104h may receive different bias values. The bias value applied to a given bias region may depend on the intended application of the device and the determined behavior of CMUTs within that bias region.

Figure 5:
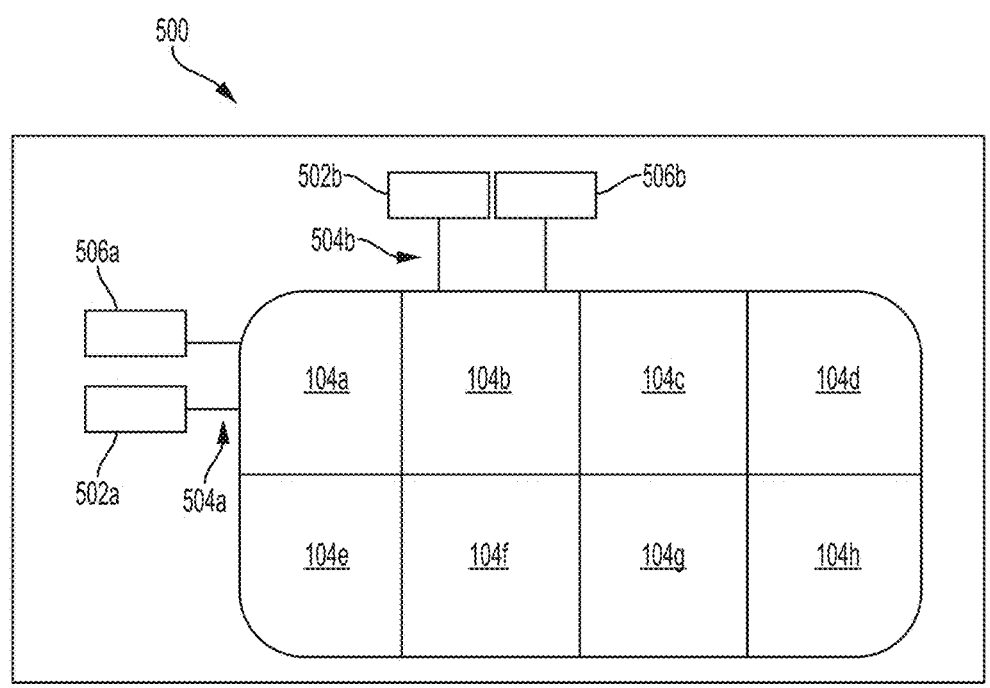
FIG. 5 is a top-down view of an ultrasound device of the type illustrated in FIG. 1 together with a plurality of voltage sources and detection circuits, according to a non-limiting embodiment.

Accordingly, an aspect of the present application provides circuitry and methods for determining a bias value to apply to a bias region of an ultrasound device. Referring to FIG. 5, the device 500 is similar to the device 100 of FIG. 1, but additionally includes a plurality of voltage sources and a plurality of detection circuits. Voltage source 502a is coupled to bias region 104a to provide a bias signal via bias line 504a. The bias signal may be applied and a response from the CMUTs of that bias region may be detected by detection circuit 506a. The response may be an electrical response. Depending on the detected response, it may be determined that the bias signal should be altered to achieve desired CMUT operation. Similarly, with respect to bias region 104b, a bias signal may be applied by voltage source 502b via bias line 504b, and a response detected by detection circuit 506b. The value of the applied bias signal may be adjusted as necessary to achieved desired CMUT operation.

While FIG. 5 illustrates voltage sources and detection circuits only for bias regions 104a and 104b, it should be appreciated that a voltage source and detection circuit may be provided for each bias region. The detection circuits may be implemented as integrated circuitry 208 in some embodiments. Also, alternative configurations to that of FIG. 5 are possible. For example, a single voltage source may be provided for all the bias regions, with suitable circuitry to adjust the voltage provided by the voltage source to values specific for each of the bias regions (e.g., voltage dividers, amplifiers, etc.). More generally, the device 500 may be a single substrate device, with all the illustrated components monolithically integrated on the same substrate. Alternative configurations, including multi-chip configurations, are possible.

The described operation of detecting CMUT behavior and adjusting an applied bias signal may be performed at limited times in some embodiments. For example, determination of the appropriate bias voltage may be determined once, after manufacture, according to one embodiment. In this sense, the determination of the appropriate bias voltage may be considered a calibration step in manufacturing. In some embodiments, the determination may be performed periodically to account for device aging, for example after a set number of uses of the ultrasound device 500. In some embodiments, the determination may be performed dynamically during operation of the ultrasound device 500.

While FIGS. 1 and 5 illustrate eight bias regions, it should be appreciated that other numbers of bias regions may be provided. For example, in some embodiments, more than two bias regions may be provided. In some embodiments, between two and twelve bias regions may be provided, any number within that range, or more. The more bias regions provided, the greater the ability to provide a bias signal appropriately tailored to a specific group of CMUTs. However, a greater number of bias lines may also be needed, which can take up space and increase wiring complexity. Thus, a balance may be struck.

Also, while FIGS. 1 and 5 illustrate bias regions which are substantially rectangular, the present application is not limited in this respect. Bias regions may assume any suitable shape and any suitable placement relative to each other.

It should be appreciated from the foregoing that an aspect of the present application provides a method for biasing CMUTs of an ultrasound device. The method may include electrically biasing at a first bias voltage a first bias electrode corresponding to a first group of ultrasonic transducers and, simultaneously with biasing the first bias electrode, electrically biasing at a second bias voltage different than the first bias voltage a second bias electrode corresponding to a second group of ultrasonic transducers. Electrically biasing the first bias electrode may involve electrically biasing a common membrane of a plurality of CMUTs.

Optionally, in response to electrically biasing the first bias electrode, an electrical response of the first group of ultrasonic transducers may be detected and the bias signal may be altered. The first bias voltage may be up to approximately 30% greater than the second bias voltage, or may differ from the second bias voltage by any of the percentages previously listed herein.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

As a non-limiting example, various embodiments have been described as including CMUTs. In alternative embodiments, piezoelectric micromachined ultrasonic transducers (PMUTs) may be used instead of, or in addition to, CMUTs.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasound device, comprising:
   a substrate;
   a plurality of ultrasonic transducers integrated with the substrate and including a first group of ultrasonic transducers and a second group of ultrasonic transducers; and
   a plurality of individually electrically controllable bias electrodes including:
   a first bias electrode corresponding to the first group of ultrasonic transducers and comprising a first common membrane of the first group of ultrasonic transducers; and
   a second bias electrode corresponding to the second group of ultrasonic transducers and comprising a second common membrane of the second group of ultrasonic transducers.

2. The ultrasound device of claim 1, wherein the first group of ultrasonic transducers are capacitive micromachined ultrasonic transducers.

3. The ultrasound device of claim 2, wherein the substrate is a semiconductor die, and wherein the capacitive micromachined ultrasonic transducers are monolithically integrated with the semiconductor die.

4. The ultrasound device of claim 2, wherein the substrate has a device surface with a width between approximately 20 mm and approximately 40 mm and a height between approximately 2 mm and approximately 10 mm, and wherein the plurality of individually electrically controllable bias electrodes includes between four bias electrodes and ten bias electrodes corresponding to respective groups of the plurality of ultrasonic transducers.

5. The ultrasound device of claim 2, further comprising a plurality of bias lines corresponding to the plurality of individually electrically controllable bias electrodes and including a first bias line coupled to the first bias electrode and a first power supply and a second bias line coupled to the second bias electrode and a second power supply.

6. The ultrasound device of claim 1, further comprising a detection circuit integrated with the substrate and configured to detect an electrical response of the first group of ultrasonic transducers.

7. The ultrasound device of claim 1, further comprising an integrated circuit integrated with the substrate and coupled to the first and second groups of ultrasonic transducers.

8. A method of operating an ultrasound device having a substrate and a plurality of ultrasonic transducers integrated with the substrate, the method comprising:
   electrically biasing at a first bias voltage a first bias electrode comprising a first common membrane corresponding to a first group of ultrasonic transducers of the plurality of ultrasonic transducers; and
   simultaneously with biasing the first bias electrode, electrically biasing at a second bias voltage different than the first bias voltage a second bias electrode comprising a second common membrane corresponding to a second group of ultrasonic transducers of the plurality of ultrasonic transducers.

9. The method of claim 8, wherein the first group of ultrasonic transducers are capacitive micromachined ultrasonic transducers.

10. The method of claim 8, further comprising, in response to electrically biasing the first bias electrode, detecting an electrical response of the first group of ultrasonic transducers.

11. The method of claim 8, wherein the first bias voltage is up to approximately 30% greater than the second bias voltage.

12. The method of claim 8, wherein electrically biasing the first bias electrode is performed using an integrated circuit integrated with the substrate.

\* \* \* \* \*